US006992235B2

(12) United States Patent
Bode et al.

(10) Patent No.: US 6,992,235 B2
(45) Date of Patent: Jan. 31, 2006

(54) METHOD FOR MARKER-FREE REPETITIVE DNA EXPRESSION CASSETTE EXCHANGE IN THE GENOME OF CELLS OR PARTS OF CELLS

(75) Inventors: Jürgen Bode, Braunschweig (DE); Jost Seibler, Braunschweig (DE); Dirk Schübeler, Braunschweig (DE)

(73) Assignee: Gesellschaft fur Biotechnologische Forschung mbH, Braunschweig (DE)

( * ) Notice: Subject to any disclaimer, the term of this patent is extended or adjusted under 35 U.S.C. 154(b) by 0 days.

(21) Appl. No.: 09/841,843

(22) Filed: Apr. 25, 2001

(65) Prior Publication Data

US 2001/0032341 A1 Oct. 18, 2001

Related U.S. Application Data

(63) Continuation of application No. 09/257,561, filed on Feb. 25, 1999, now abandoned.

(30) Foreign Application Priority Data

Feb. 27, 1998 (EP) .......................................... 98 103 490

(51) Int. Cl.
*C12N 15/00* (2006.01)
*C12N 5/00* (2006.01)
*C12N 15/09* (2006.01)

(52) U.S. Cl. ........................ 800/21; 800/25; 435/320.1; 435/325

(58) Field of Classification Search ................... 800/21, 800/25, 8; 435/320.1, 325
See application file for complete search history.

(56) References Cited

U.S. PATENT DOCUMENTS 5,654,182 A * 8/1997 Wahl et al. .............. 435/172.1

FOREIGN PATENT DOCUMENTS

WO      WO 97/47758        12/1997

OTHER PUBLICATIONS

Seamark "Progress and Emerging . . . " Reprod Fertil Dev 6:653–657 (1994).*
Moreadith et al. Gene Targeting in embryonic . . . J Mol Med 75:208–216 (1997).*
Jung et al. "Shutdown of Class Switch . . . " Science 259: 984–987 (1993).*
Ludwig et al. "FLP–mediated stie–specific . . . " Trans Res 5:385–395 (1996).*
Bethke et al. "Segmental genomic replacement . . . " NAR 25(14):2828–2834 (1997).*
Schlake et al. "Use of mutated FLP . . . " Biochemistry 33:12746–12751 (1994).*
J. Seibler et al., "DNA Cassette Exchange in ES Cells Mediated by FLP recombinase: An Efficient Strategy for Repeated Modification of Tagged Loci by Marker–Free Constructs", Biochemistry, (May 5, 1998) vol. 37, No. 18, pp. 6229–6234, XP–02074112.
J. Seibler et al., "Double–Reciprocal Crossover Mediated by FLP–Recombinase: A Concept and an Assay", Biochemistry, (Feb. 18, 1997), vol. 36, No. 7, pp. 1740–1747, XP–002074110.
T. Schlake et al., "Use of Mutated FLP Recognition Target (FRT) Sites for the Exchange of Expresson Cassettes at Defined Chromosomal Loci", Biochemistry, (Nov. 1, 1994) vol. 33, No. 43, pp. 12746–12751, XP–000616165.
H. Wu et al., "Double replacement: Strategy for efficient introduction of subtle mutations into the murine *Colla–1* gene by homologous recombination in embryonic stem cells", PNAS, U.S.A., vol. 91, No. 7, (Mar. 29, 1994), pp. 2819–2823, XP–002074111.
S. Karreman et al., "On the use of double FLP recognition targets (FRTs) in the LTR of retroviruses for the construction of high producer cell lines", Nucleic Acids Research, 1996, vol. 24, No. 9, (May 1, 1996), pp. 11616–11624, XP–000616161.

* cited by examiner

*Primary Examiner*—Joseph Woitach
(74) *Attorney, Agent, or Firm*—Brooks Kushman P.C.

(57) ABSTRACT

The invention relates to a method for marker-free DNA expression cassette exchange in the genome of cells or parts of cells by using the FLP recombinase mediated cassette exchange. A first DNA expression cassette carrying a positive-negative selection marker flanked by two FLP recombinase recognition target (FRT) sites is integrated into a chromosomal locus of the genome. Following selection of cell clones surviving the conditions for positive selection, the first DNA cassette is exchanged by an incoming second DNA expression cassette located on a circular vector and carrying a transgene flanked by the same FRT sites as the first DNA cassette by using FLP-recombinase. The cell clones surviving the conditions for negative selection contain specifically inserted the gene of the incoming DNA cassette without inserted unwanted vector sequences or positive selectable markers.

4 Claims, 3 Drawing Sheets

1. *Tag*
Introduction of a plus/minus selection marker
- by homologous recombination into a defined locus
- by random integration 2. *Exchange*
Replacement of the plus/minus selection marker by the sequence of interest

*Exchange:*
FLP recombinase + selection,
- with GANC
- or G418
- or G418 + GANC

METHOD FOR MARKER-FREE REPETITIVE DNA EXPRESSION CASSETTE EXCHANGE IN THE GENOME OF CELLS OR PARTS OF CELLS

This is a continuation of application(s) Ser. No. 09/257,561 filed on Feb. 25, 1999 now abandoned.

The invention relates to a method for marker-free repetitive DNA expression cassette exchange in the genome of cells or parts of cells, to regenerative vertebrate cells or nuclei of such cells comprising a modified genome obtainable by said method and a method for the generation of transgenic vertebrates by injecting such regenerative vertebrate cells into blastocystes of said vertebrates.

The availability of techniques for generating transgenic mice from genetically modified embryonic stem (ES) cells provides a means to analyze specific gene functions or cis-regulatory DNA elements in normally developing mammals. So far, most studies (it should be noted that in the following all numbers in parenthesis shall refer to the bibliography at the end of the description) have created null mutations in order to assay the function of a gene product. During such a "knock-out" experiment a coding region is replaced or disrupted by a selectable marker gene using homologous recombination techniques. Current extensions of this approach are aimed at more subtle, multiple and independent changes either in the gene product or the DNA sequences regulating the locus, a concept referred to as a "knock-in".

Efficient repetitive modification of a particular genomic locus is desired not only in association with homologous re-combination (HR) to introduce subtle mutations in a known locus, but also for randomly integrated constructs where the expression characteristics of each integration site can be exploited to express transgenes in a defined and predictable manner. So far, the study of cis-regulatory elements that are randomly integrated into cell lines has been limited by the powerful effects of genomic position on transcription of the integrated construct. Transient transfection, the available alternative, is clearly unable to analyze elements that are functional only after integration into the genome (1). Every advanced strategy for introducing secondary modifications into predefined loci is based on first tagging the locus with a selectable marker which is done by homologous recombination (HR). Once the initial tag has been inserted there are systems available that facilitate secondary modifications to the site using the tag as target, but each of these systems has certain limitations.

Limitations of present systems and how they are remedied. Two types of procedures have been described for repetitive modifications of genomic loci; one is based on HR (PNAS USA, 90 (1993) 8469–8473), and the other on site-specific recombination (SR). In the first case, the efficiency is limited by the frequency of the HR, which differs widely among loci and cell lines. Moreover, common procedures like the "plug-and-socket" approach (2) leave behind a selectable marker causing a potential problem since an increasing number of examples is reported where the presence of an expressed selectable marker deregulates a locus (3–5b and references therein).

Finally, HR cannot be used for modifying sites tagged by random integration unless these have been cloned and characterized.

Published methods based on SR circumvent some of these limitations. Up to now, however, all SR-based systems also leave behind a selectable marker and, if a single recombinase site is used as a target, unwanted vector sequences are inserted. The technical goal we have pursued here and an object of the invention is the development of an SR-based strategy for making repeated modifications to a given locus that would have the following characteristics: 1—no requirement for an incoming selectable marker; 2—independence of HR; 3—no insertion of vector sequence; 4—high efficiency; 5—functional in different genomic locations.

Accordingly, the invention relates to a method for marker-free repetitive DNA expression cassette exchange in the genome of cells or parts of cells as defined in claim 1.

Moreover, the invention relates to regenerative vertebrate cells and nuclei of vertebrate cells comprising a modified genome obtainable by a method of the invention as per claims 7 and 8, respectively, and regenerative vertebrate cells containing such nuclei with a modified genome as per claim 9 and a method for the generation of transgenic vertebrates by injecting regenerative vertebrate cells into blastocystes of said vertebrates as per claim 10.

Further advantageous and/or preferred embodiments of the invention are subject matter of the subclaims.

The abovementioned requirements can be met by FLP recombinase in conjunction with sets of heterospecific FLP recombinase target (FRT-) sequences. FLP-recombinase is originally coded by the $2\mu$ plasmid of *Saccharomyces cerevisiae* and performs powerful site-specific recombination reactions. Using an incoming positive selection marker the principle has previously been used for FLP (6, 7) or, more recently, for the Cre recombinase (8, 9) and it is now commonly termed "recombinase mediated cassette exchange" (RMCE).

The RMCE reaction. Recombinases such as FLP and Cre have emerged as powerful tools to manipulate the eukaryotic genome (10, 11). These enzymes mediate a recombination between two copies of their target sequence and have mainly been used for deletions. We show here that FLP-RMCE can be applied to introduce secondary mutations at a locus which has been previously tagged by a positive/negative selectable marker, and that these secondary mutations can be produced without depending on a selectable marker on the incoming DNA. FPL-RMCE utilizes a set of two 48 bp FLP target sites, in this case wild type (F) and $F_3$, a mutant that was derived from a systematic mutagenesis of the 8 bp spacer localized between the FLP binding elements (6). FLP effects recombination between the $F_3/F_3$ couple which is as efficient as between the wild type sites (F/F) but it does not catalyze recombination between a F/$F_3$ pair (7). Thereby FLP-RMCE enables the specific exchange of an expression cassette in the genome which is flanked by a $F_3$-site on one end and a F-site on the other for an analogous cassette comprising virtually any sequence which is provided on a plasmid in a single step without the need of introducing a positive selectable marker (FIG. 1). Nothing else in the genome is altered and no plasmid sequences are inserted. In contrast to approaches using a single recombination site the targeting product is stable even under the permanent influence of the recombinase unless it is exposed to an exchange plasmid (7). The system can be used to analyze the function of either a gene product or of regulatory sequences ES-cells or the derived transgenic mice.

Here, we report use of FLP-RMCE to modify random genomic loci in ES cells. In all three individual sites examined, this modification can be efficiently done by only selecting for the loss of the hygtk positive/negative selectable marker (FIG. 1B). Since there is no functional requirement for the incoming DNA, except for the two different FRT-sites, this strategy permits an efficient marker free targeting of a tagged locus in a single step.

EXAMPLES AND MATERIALS AND METHODS

Figure 1A:
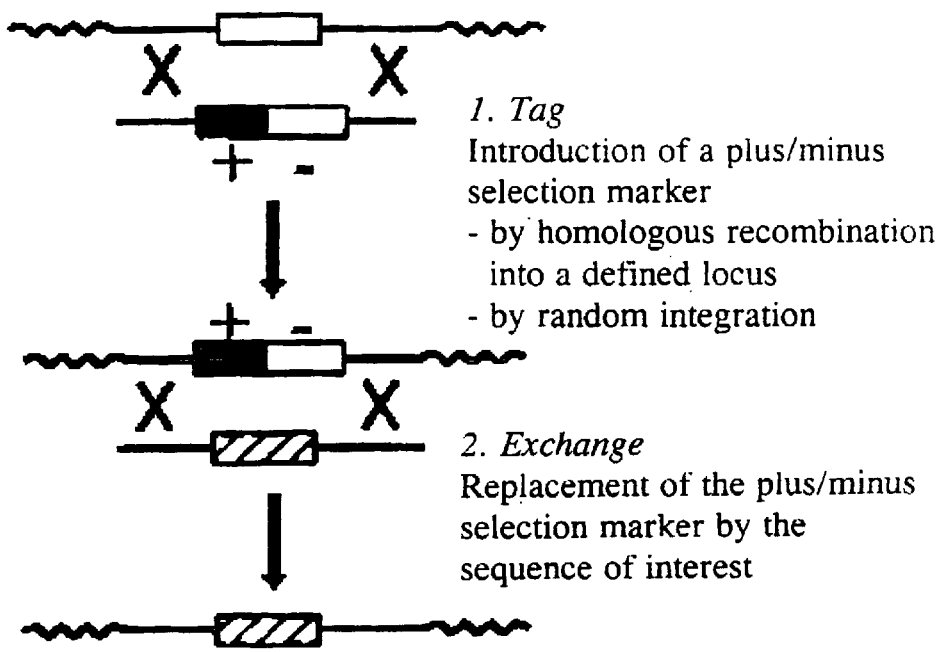
FIG. 1. (A) Outline of a tag and exchange experiment. (B) Use of the FLP-RMCE to exchange a genomically anchored plus/minus selection marker (hygtk) for an expression cassette. This can be done by only selecting against the presence of the negative marker, by only positive selection and by a combination of both. Half arrows mark the positions of heterospecific FRT-sites (solid, wild type; light, mutant $F_3$). Circles next to the $F_3$ site indicate two copies of the polyoma enhancer (see Materials and Methods).

Plasmids. Construction of plasmids $F_3$hygtkF and $F_3$neoF followed the procedures for $F_5$hygtkF and $F_5$neoF (6). For $F_3$ the wild type FRT spacer sequence (TCTAGAAA) was changed to TtcAaAtA. The hygtk gene in $F_3$hygtkF is driven by the HSV-tk promoter and two copies of the polioma enhancer, which together confer robust expression in ES-cells (12). The neo$^r$ gene in $F_3$neoF is under the control of the HSV-tk promoter only and yields no G418 resistant clones. Therefore a different construct, $F_3P^{pgk}$neoF had to be used for positive selection in which the neo$^r$ gene is controlled by the pgk-promoter, isolated from pgkneobpA (a gift of Phil Soriano, Seattle, not critical to carry out the invention).

Cell culture and transfection. Murine ES cells (CCE) were cultured in DME medium containing 15% FCS, $10^4$ U/ml LIF (BRL) and 1,75 ng/ml monothioglycerol. Cells were grown without feeders on dishes coated with 0.1% gelatine. For transfection, semiconfluent cells were dispersed with trypsin. $3 \times 10^6$ cells were collected and electroporated with the appropriate plasmid(s) at 500 $\mu$F and 250 V/cm in a BioRad gene pulser. Electroporated cells were seeded on four 100 mm dishes.

Cell lines with a single copy "tag". To obtain independent integration events of $F_3$hygtkF, cells were electroporated with 10 $\mu$g of the linearized plasmid and medium containing 167 U/ml hygromycin (HYG) (Calbiochem) was added the next day. Clones were isolated ten days post transfection.

RMCE. 100 $\mu$g of recombinase expression plasmid flp-F70L (13), and 30 $\mu$g of $F_3$neoF (or $F_3P^{pgk}$neoF) were co-electroporated as circular plasmids into cell clones with a single copy of $F_3$hygtkF. Negative selection (ganciclovir, GANC) was applied on day 4 or 5. Cells were seeded one day prior to selection at low densities ($10^5$ per 100 mm dish) to avoid metabolic cross-feeding. Clones were isolated between day 8 and 10. For $F_3P^{pgk}$neoF, RMCE-modified clones could be enriched by negative and/or by positive selection. Positive selection was done in the presence of G418 (500 $\mu$g/ml, GIBCO) one day after electroporation. For positive plus negative selection GANC selection started when the first G418 resistant clones emerged (after about 7 days).

Genomic DNA. Genomic DNA was prepared according to (14) with small modifications. ES-cells were harvested from 24-well plates and Proteinase K digestion and DNA precipitation was performed in 1.5 ml tubes. Southern and Northern blotting procedures followed (15).

RESULTS

Tagging different loci. Our experiments are based on a target construct, $F_3$hygtkF, containing the hygtk fusion gene which encodes both hygromycin-B-phosphotransferase and HSV-thymidine kinase (HSV-Tk) activities. This marker allows positive selection for hygromycin (HYG) resistance and negative selection in the presence of gancilovir (GANC), which is converted into a cytotoxic drug in the presence of HSV-Tk. The hygtk cassette is flanked by a wildtype FRT site (F) and a mutant ($F_3$) which together permit the application of the RMCE principle (FIG. 1B). $F_3$hygtkF was introduced into CCE embryonic stem cells by electroporation and 22 HYG resistant clones were individually analyzed for the number of integrated copies. 15 clones revealed a unique bordering fragment and five of these were further analyzed for the integrity of the insert (data not shown). Two clones showed evidence of a deletion at the 3' end and were omitted from the study. The three remaining unique clones (F18, F21 and F22) served as targets for the RMCE reaction (Tab. 1).

TABLE 1

Targeting efficiency. Number and frequency of targeted clones, isolated from $10^5$ cells by negative selection.

| Clone | F18 | F21 | F22 | Exchange construct |
|---|---|---|---|---|
| GANC$^R$ colonies |  | 24 | 63 | $F_3$neoF |
|  | 16 |  |  | $F_3P^{pgk}$neoF |
| Clones analysed | 16 | 24 | 26 |  |
| Clones targeted | 6 | 5 | 6 |  |
| Targeting frequency (%) | 38 | 21 | 23 |  |

Figure 2A:
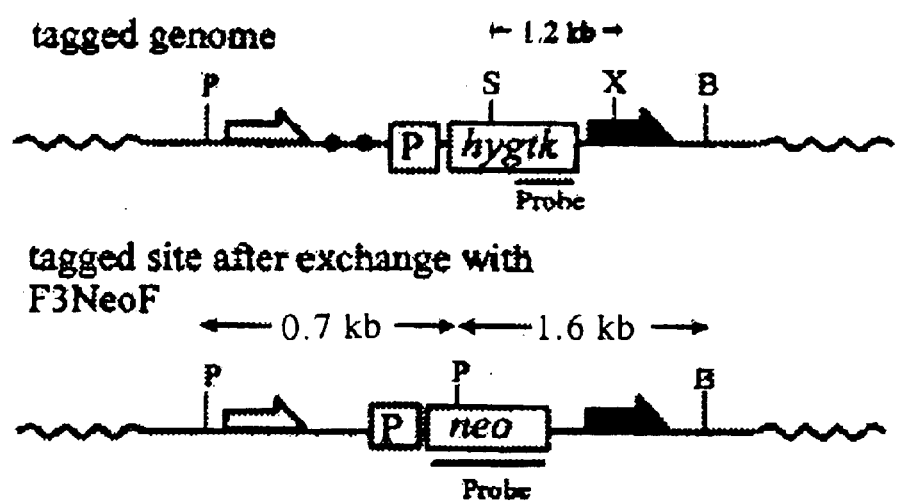
FIG. 2. Analysis of GANC$^r$ clones arising from FIG. 1B-type experiments. (A) Restriction maps of a tagged locus before and after the exchange. The hygtk and the neo-constructs contain the HSV-tk-promotor (P) but only hygtk contains two copies of the polioma enhancer elements in addition. Cleaveage sites: SphI (S), XbaI (X), BglI (B), PvuII (P). (B) The DNA of the clones was digested at the S and X sites (upper) or B plus P sites and analyzed on a Southern blot. Lanes 1, 3 and 6 show clones resulting from spontaneous inactivation of the hygtk-gene and lane 7 the parental clone. The 0.7 and 1.6 kb bands expected for an authentic cassette exchange are found in lanes 2, 4 and 5.
Figure 2B:
Figure 2B:
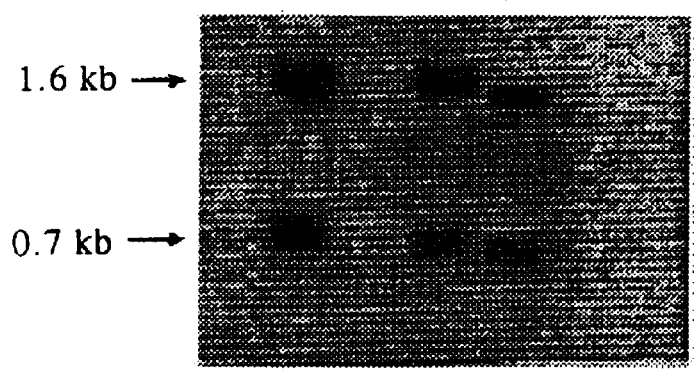

RMCE enriched by negative selection. The exchange vector ($F_3$neoF or $F_3P^{pgk}$neoF) was transfected together with the recombinase expression construct (flp-F7OL), both in circular form. Circularity is required for transient expression in ES-cells and it also reduces the possibility of random integration. Selection with GANC for the loss of the hygtk gene product yielded 16–63 resistant subclones from each of the three clonal lines (Tab. 1) which were analyzed for a successful exchange of the hygtk by the neo$^r$ cassette on Southern blots. Hybridization with a mixture of neo$^r$ and tk probes revealed 1.6 and 0.7 kb fragments for subdones in which RMCE had taken place and a 1.2 kb fragment if it had not (FIG. 2).

Analysis of subclones with a spontaneous resistance to GANC. Cells surviving the GANC selection have lost Tk activity, either by the RMCE, by spontaneous inactivation or loss of the gene. If only negative selection is utilized, the spontaneous loss of Tk activity determines the background of resistant non-RMCE clones. An analysis revealed two types of background colonies:

1) All subclones derived from F21 and F22 still revealed a complete copy of the hygtk gene on Southern blots. Northern blot analyses showed that while the parental F21 and F22 clones produced detectable amounts of the hygtk transcript the investigated subclones did not (data not shown). Therefore, epigenetic inactivation of expression appears to be one source of clones which survive the selection but retain the hygtk gene.

2) $GANC^r$ subclones from F18 showed no Southern blot signal for the hygtk gene. Such a result would be expected for a crossrecombination between the two heterospecific FRT-sites (F and $F_3$) or for a physical loss by chromosomal aberration. To resolve these alternatives, the blots were reprobed with a fragment from the vector backbone upstream of the $F_3$-site which would yield a specific 250 bp PvuII-BglI signal in case of a crossrecombination. The lack of any signal in these clones strongly suggests the loss of the whole vector and excludes a crossrecombination between F and $F_3$. Therefore, for this clone GANC resistance in the absence of RMCE is ascribed to chromosomal aberration as reported in previous repetitive modification studies (16, 17).

Background resistance is reduced by selection for Hygtk. As loss of the Hygtk enzymatic activity is the source of GANC resistance in the absence of RMCE, we tested ten different clones harboring a single copy of $F_3$hygtkF for their propensity to become spontaneously resistant during their expansion in non selective medium (i.e. prior to GANC selection). Under the conditions specified in the Table 2 legend the clones chosen for RMCE (F18, F21, F22) and an additional one (F8) maintained sensitivity towards GANC showing that in these cases Hygtk inactivation is minimal. Others varied widely in this respect, reflecting the different characteristics of the integration sites.

Since our study is based on a fusion gene which permits positive or negative selection, loss of Tk and hygromycin-B-phosphotransferase activities should be linked. Therefore inactivated clones should not accumulate during positive selection. To verify this assumption six parental clones which were prone to spontaneous resistance were expanded either in non-selective medium as above or in a medium containing HYG. Tab. 2 demonstrates that three clones yielded no $GANC^r$ subclones if they were cultivated in the presence of HYG. For F5 the number of clones was reduced fiftyfold and for the remaining ones six or threefold, respectively.

Tab. 2. Spontaneous resistance. Number of spontaneously resistant clones arising from $10^4$ cells after ganciclovir (GANC) selection over 7 days. −HYG: cells have been cultivated in normal medium prior to GANC selection. +HYG: cells have been cultivated for 4 passages in the presence of hygromycin (HYG) prior to GANC selection.

These data clearly demonstrate that the rate and mode of inactivation is unpredictable for a given locus. However, the accumulation of inactivated clones prior to negative selection can be significantly reduced if a fusion enzyme harboring positive and negative selectable activities is used and positive selection is maintained during cultivation prior to negative selection.

RMCE enriched by positive selection. We next utilized the encoded activity of the $neo^r$ gene to study details of the exchange reaction and to test the efficacy of FLP-mediated RMCE when positive selection for the incoming marker is applied. This marker was provided on a construct ($F_3P^{pgk}neoF$) which mediated expression of the neomycine resistance gene in ES cells. Although negative selection is to be preferred wherever feasible, the application of a positive selection system expands the RMCE to sites that either give a high level of spontaneous GANC resistance or are not tagged with a positive/negative selectable marker gene. Therefore the same three clonal lines used above were selected with G418 after electroporation of the FLP expression plasmid and $F_3P^{pgk}neoF$.

Figure 3:
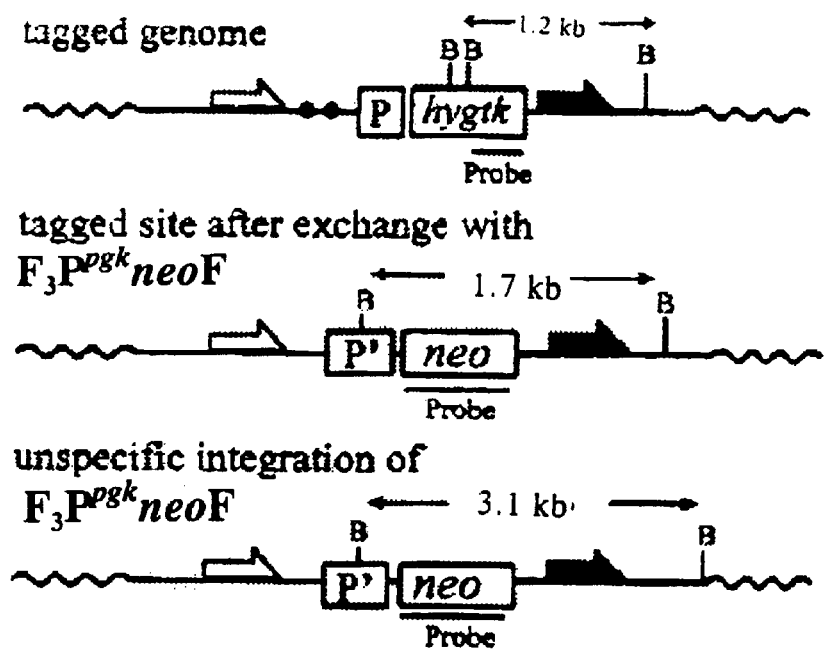
FIG. 3. Analysis of G418 and G418/GANC-resistant sub-clones arising from clone F18. (A) Restriction maps of a tagged locus of parent clones and subclones resulting from the exchange (B, BglI). Here the neo$^r$-gene is driven by the pgk-promotor ($p^{pgk}$). (B) Southern blots of BglI digests. Lanes 1 to 5 show clones resulting from G418 selection. Persistance of the hygtk-gene is documented by the 1.2 kb signal while the 3.1 kb signal derives from a randomly integrated copy of $F_3P^{pgk}$neoF. Only the exchange leads to an exclusive 1.7 kb signal. Lanes 6 to 9 derived from clones after G418/GANC selection which all underwent the exchange.
Figure 3:
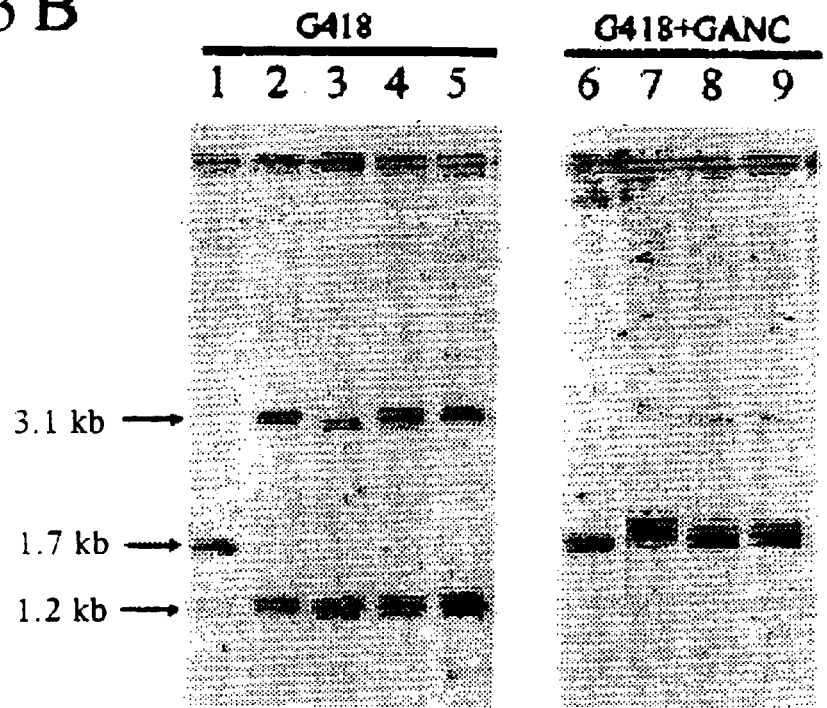

Subclones were obtained by G418 and G418 plus GANC double selection (Tab. 3) and characterized as illustrated in FIG. 3. RMCE positive clones yield a 1.7 kb fragment if hybridized with a $neo^r$ probe. When reprobed with a tk sequence, the absence of a 1.2 kb band verifies the complete exchange. In selection only with G418, two classes of subclones were observed. Class 1 exhibited a 1.2 kb signal for the tk probe and a 3.1 kb (but no 1.7 kb) signal for the $neo^r$ probe: the 1.2 kb fragment shows persistence of the $F_3$hygtkF tag while the 3.1 kb band results from a random integration of the complete $F_3P^{pgk}neo'F$ construct (FIG. 3). Class 2 (25% of investigated clones) had undergone the authentic exchange as documented by the presence of an 1.7 kb $neo^r$ signal and the absence of the 1.2 kb tk signal. In no case did we observe a recombination at a single FRT site with retention of the hygtk gene, a possible result when selection only for G418 resistance is applied. This suggests either that RMCE intermediates which would arise from singular recombination events at the F or $F_3$ sites (6) are efficiently resolved by F/F or $F_3/F_3$ recombination, or that RMCE occurs via a simultaneous double-crossover mechanism as diagrammed in FIG. 1B.

With positive selection only, the efficiency of RMCE was 6% for F21, 24% for F18 and 50% for F22 (Tab. 3). This difference between the sites may reflect the characteristics of the different chromosomal locations of the hygtk tag or a different probability of random integration for the four clones. On the other hand, the targeting efficiency for positive plus negative double selection was either 54 or 100% (Tab. 3). Such an improvement arises because clones which owe their G418 resistance to a randomly integrated copy still contain the hygtk gene and are therefore eliminated with GANC.

|      | F8    | F18   | F22   | F21   | F1 | F5  | F9   | F19 | F20 | F23 |
|------|-------|-------|-------|-------|----|-----|------|-----|-----|-----|
| −HYG | 0     | 0     | 0     | 0     | 30 | 100 | 1000 | 500 | 20  | 40  |
| +HYG | n. d. | n. d. | n. d. | n. d. | 0  | 2   | 300  | 80  | 0   | 0   |

TABLE 3

Number and frequency of clones obtained using positive and positive plus negative selection.

| Clone | F18 | F21 | F22 | neo-construct |
|---|---|---|---|---|
| G418$^r$ colonies | 38 | 24 | 2 | FP$^{pgk}$neoF |
| Clones analysed | 17 | 16 | 2 | |
| Clones targeted | 4 | 1 | 1 | |
| Targeting frequency (%) | 24 | 6 | 50 | |
| G418$^r$ + GANC$^r$ colonies | 4 | 20 | 21 | FP$^{pgk}$neoF |
| Clones analysed | 4 | 13 | 14 | |
| Clones targeted | 4 | 7 | 14 | |
| Targeting frequency (%) | 100 | 54 | 100 | |

DISCUSSION

We have demonstrated the efficient recombinase mediated exchange of a cassette that has been randomly integrated into the genome of ES cells for a vector-borne cassette of the same type. This exchange is achieved by the FLP-RMCE system, which does not insert plasmid sequences and does not depend on the frequency of HR. Since RMCE is possible without positive selection for the incoming vector, this system permits great flexibility in the composition of the exchange construct. This system also functions using positive selection for the incoming vector while a maximum efficiency is achieved by combining positive and negative selection. Such versatility makes FLP-RMCE unique compared to other reported systems.

Figure 1B:
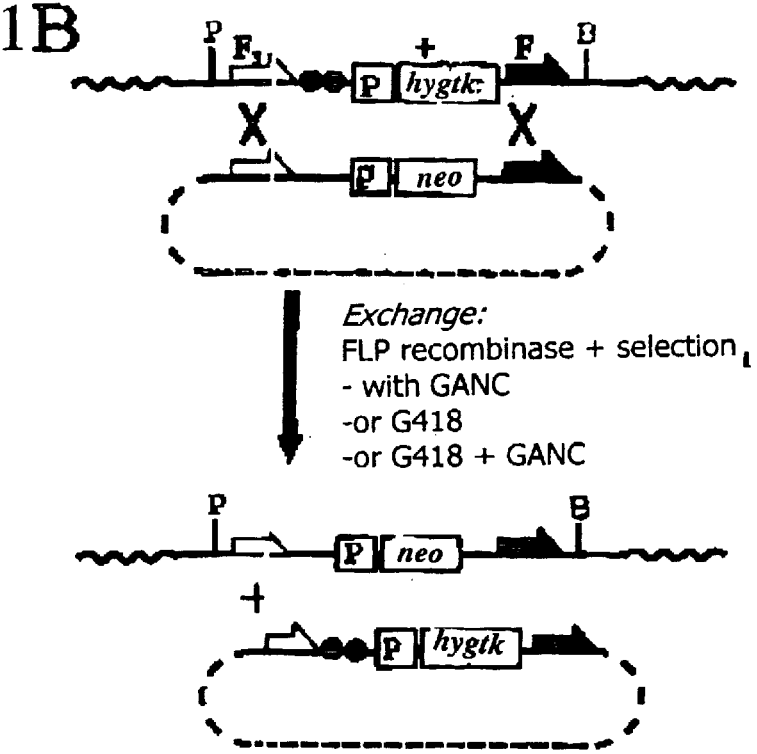

The use of HR for the marker-free targeting of an endogenous locus in ES-cells has been described previously, and has been named "tag and exchange" (16) or "double replacement" (17; see FIG. 1A). In this strategy HR was used to tag an endogenous sequence with a neo$^r$/HSV-tk gene cassette and also for the second step in which a mutation is introduced and selected for by the loss of Tk-activity. In one study (16) 1.4% of the GANC$^r$ clones were targeted correctly and in the other (17) the efficiency was 9.6%. The targeting efficiencies we have achieved at three different loci are higher and thus we anticipate that FLP-RMCE will be an improvement over existing methods. These prerequisites may aid the efficient generation of transgenic mice by injecting the modified ES cells into blastocysts (see ref. 17).

The major advantage of FLP-RMCE is the ability to introduce a marker-free construct independent of HR. During the preparation of this manuscript two papers appeared which applied Cre based exchange systems with heterospecific lox-sites to cell lines other than ES cells (8, 18). These studies elaborate Cre-RMCE, a system comparable to FLP-RMCE, but they depend on a positive selection "trap" system in which only the correct targeting event reconstitutes the selected marker. A trap strategy has been reported previously for the modification of ES cells where it was based on HR and therefore restricted to known loci (2).

As a prerequisite for the exclusive use of negative selection the background of GANC resistant clones has to be low. This demands the lack of FLP-mediated crossrecombination between the recombinase targeting sites constituting a set (here: F and F$_3$) which would excise the negative marker and lead to subclones that survive negative selection without having the exchange. None of the clones we analyzed in this study had undergone such crossrecombination. The experiments reported for Cre-RMCE do not address the question of a possible crossrecombination, because a product of such reaction yields no surviving clone if a selection trap is used. It will be interesting to learn if the experimental strategy reported here will also be possible for Cre with the currently used loxP mutant which was derived from a point mutation in the spacer (19) or for any other potential heterospecific loxP sites.

A background due to spontaneously resistant clones is inherent in any targeting system based on the exclusive use of negative selection, irrespective of whether SR or HR is used (16, 17). In the clones we analyzed this background was governed by the frequency at which expression of the hygtk gene is silenced or by the loss of the construct by chromosomal aberration. We demonstrate that employing HYG-selection and thereby enforcing expression of the hygtk gene up to the time-point of negative selection is well suited to reduce the accumulation of inactivated clones (Tab. 2). Our data also indicate that there exist genomic locations for which RMCE based on negative selection will be inefficient, and it will require extensive further work to determine the frequency at which silencing of the gene or loss of the construct events require to enrich RMCE by a positive selectable marker.

In cases where RMCE events are enriched by negative selection, the selectable marker is removed during the exchange step and thereby reusable for further manipulations. Since there is only a restricted number of selectable markers available for manipulating murine embryonic stem cells this may be an advantage of its own (20). FLP-RMCE requires that the set of FRT sites (F and F$_3$) is present in the genome before and after the exchange. There is no data to suggest that the 48 base pair FRT sites have any activity other than those associated with FLP recombination, and even their insertion between triplet codes conserves a gene's reading frame and expression (21). Their position within the locus must nevertheless be accounted for by the design of any experiment. For random integration sites this does not cause any restriction, but for HR tagged sites care must be taken that FRT sites are situated so as not to interfere with the coding regions of an inserted or endogenous gene.

If the initial tagging is performed by HR the system permits the introduction of subtle mutations in an endogenous locus or gene product. Performing the initial tagging by random integration allows the selection of tagged expression sites in ES-cells for repeated use either to compare different cis-regulatory elements or to construct transgenic mouse lines that express the protein of interest at reproducible levels and in the appropriate tissues. Position effects are a frequent obstacle to this goal, and often the tendency to silence varies according to tissue type. In cases where an expression pattern is specific for some restricted cell type for which no cis-regulatory elements are known, RMCE will permit the identification of appropriately regulated and stable genomic sites which can then be used for a reproducible expression of a construct in the tissue of interest.

The manipulation of ES cells and the subsequent analysis of transgenic mice has led to important insights into gene function and regulation. The development of animal models for human diseases as well as the dissection of gene action and regulation will require combinations of existing and new techniques (9). By necessity, gene targeting experiments subject ES cells to long-term culture during which a progressive loss of totipotency may occur. We demonstrate here that using FLP-RMCE two subcloning steps are sufficient to set a genomic tag and to retarget it efficiently without selection for the incoming DNA. This may represent an important addition to the currently available techniques for repetitive genomic site modification.

Bibliography
1. Bode, J., Stengert-Iber, M., Schlake, T., Kay, V. & Dietz-Pfeilstetter, A. (1996) Crit. *Rev. Eukaryot. Gene Expr.* 6, 115–138.
2. Detloff, P. J., Lewis, J., John, S. MW. M., Shehee, W. R., Langenbach, R., Maeda, N. & Smithies, O. (1994) *Mol. Cell. Biol.* 14, 6939–6943.
3. Kim, C. G., Epner, E. M., Forrester, W. C. and Groudine, M. (1992) *Genes and Dev.* 6, 928–938.
4. Fiering, S., Epner, E., Robinson, K., Zhuang, Y., Telling, A., Hu, M., Martin, D. I. K., Enver, T., Ley, T. T. & Groudine, M. (1995) *Genes Dev.* 9, 2203–2213.
5. McDevitt, A., M., Shivdasani, A., R., Fujiwara, Y., Yang, D. H. & Orkin, H. S. (1997) *Proc. Natl. Acad. Sci. USA* 94, 6781–6785.
5a. Pham, C. T. N., MacIvor, D. M., Hug, B. A., Heusel, J. W. & Ley, T. J. (1996), *Proc. Nati. Acad. Sci.* 93, 13090–13095.
5b. Oancea, A. E., Berru, M. & Shulman, M. J. (1997)*Mol. Cell. Biol.* 17, 2758–2668.
6. Schlake, T. & Bode, J. (1994) *Biochemistry* 33, 12746–12751.
7. Seibler, J. & Bode, J. (1997) *Biochemistry* 36, 1740–1747.
8. Bethke, B. & Sauer, B. (1997) *Nucleic Acids Res.* 25, 2828–2834.
9. Barinaga, M. (1994) *Science* 265, 26–28.
10. Kilby, N. J., Snaith, M. R. & Murray, J. A. H. (1993) *Trends Genet.* 9, 413–421.
11. Sauer, B. (1994) *Curr. Opin. Biotechnol.* 5, 512–527.
12. Thomas, K. R. & Capecchi, M. R. (1987) *Cell* 51, 503–512.
13. Buchholz, F., Ringrose, L., Angrand, P. O., Rossi, F. & Stewart, A. F., (1996) *Nucleic Acids Res.* 24, 4256–4262.
14. Ramirez-Solis, R., Rivera-Perez, J. and Wallace, J. D. (1995) *Analyt. Biochem.* 201, 331–335.
15. Schübeler, D., Mielke, C., Maass, K. & Bode, J. (1996) *Biochemstry* 35, 11160–11169.
16. Askew, G. R., Doetschman, T. & Lingrel, J. B. (1993) *Mol. Cell. Biol.* 13, 4115–4124.
17. Wu, H., Liu, X. & Jaenisch, R. (1994) *Proc. Natl. Acad. Sci. USA* 91, 2819–2823.
18. Bouhassira, E. E., Westerman, K. & Leboulch, P. (1997) *Blood* in press.
19. Waterhouse, P., Griffiths, A. D., Johnson, K. S. & Winter, G. (1993) *Nucleic Acids Res.* 21, 2265–2266.
20. Abuin, A. & Bradley, A. (1996) *Mol. Cell. Biol.* 16, 1851–1856.
21. O'Gorman, S., Fox, D. T. & Wahl, G. M. (1991) *Science* 251, 1351–1355.

What is claimed is:

1. A method for recombinase mediated expression cassette exchange (RMCE) for substituting a positive-negative selectable marker by an incoming DNA in the genome of cells or parts of cells comprising the steps of a) integrating into a chromosomal locus of the genome of said cells a first DNA expression cassette carrying a positive-negative selection marker flanked by a wild type FLP-recombinase recognition target (FRT) site on one end and a modified heterospecific FRT site on the other end, wherein said modified heterospecific FRT site is an $F_3$ spacer mutant, b) selecting cell clones surviving the conditions for positive selection, c) exchanging said first DNA expression cassette against an incoming second DNA expression cassette located on a circular vector and carrying a homologous or heterologous gene (transgene) of any coding sequence flanked by the same FRT sites as said first DNA expression cassette mediated by the action of FLP-recombinase, wherein said cells are vertebrate embryonic stem cells (ES) and said parts of cells are nuclei of vertebrate cells, which can be inserted into ES cells, and wherein d) maintaining the conditions for positive selection during cultivation of said cells obtained in step b) for a time sufficient to exchange said first DNA expression cassette against said incoming second DNA expression cassette, e) using in step c) an incoming second DNA expression cassette which is marker-free, and f) selecting cell clones obtained after step c) surviving the conditions for negative selection, g) wherein said positive and negative selection conditions result in recombination frequencies of at least 25%.

2. The method of claim 1, wherein said positive-negative selection marker is a hygromycin-B-phosphotransferase and HSV-thymidine kinase encoding (hygtk) fusion gene.

3. The method of claim 1, wherein said vertebrate embryonic stem cells are mouse embryonic stem cells.

4. A method for generation of a chimera comprising the step of injecting mouse ES cells comprising a modified genome obtained by the method of claim 1 into the blastocysts of a mouse.

* * * * *